(12) United States Patent
Lebeau et al.

(10) Patent No.: US 9,028,547 B2
(45) Date of Patent: May 12, 2015

(54) TISSUE GRAFT FIXATION (71) Applicant: Smith & Nephew, Inc., Memphis, TN (US)

(72) Inventors: Jason Roch Lebeau, Bridgewater, MA (US); John Mahoney, Norfolk, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/690,914

(22) Filed: Nov. 30, 2012

(65) Prior Publication Data
US 2013/0090687 A1    Apr. 11, 2013

Related U.S. Application Data (62) Division of application No. 11/313,716, filed on Dec. 22, 2005, now Pat. No. 8,323,338.

(51) Int. Cl.
A61F 2/38    (2006.01)
A61B 17/04    (2006.01)

(52) U.S. Cl.
CPC ..... A61B 17/0401 (2013.01); A61B 2017/0404 (2013.01)

(58) Field of Classification Search
USPC .............. 606/72, 74, 98, 232, 233, 300, 606/319–321, 328; 623/13.11–13.17
See application file for complete search history.

(56) References Cited

U.S. PATENT DOCUMENTS 3,880,166 A    4/1975  Fogarty
4,172,330 A   10/1979  Kao
5,300,077 A *  4/1994  Howell .......................... 606/96
5,306,301 A    4/1994  Graf et al.
5,584,835 A   12/1996  Greenfield
5,645,588 A    7/1997  Graf et al.
5,733,289 A    3/1998  Seedhom et al.

(Continued)

FOREIGN PATENT DOCUMENTS

DE       4127550 A1    2/1993
WO    WO0156507 A1    8/2001
WO    WO0232345 A2    4/2002

OTHER PUBLICATIONS

First Office Action for Japanese Application No. 2008-547764, mailed Nov. 22, 2011.

(Continued)

Primary Examiner — Randy Shay
Assistant Examiner — Dinah Baria
(74) Attorney, Agent, or Firm — Wilmer Cutler Pickering Hale and Dorr LLP (57) ABSTRACT A surgical device includes a member having first and second opposing surfaces. The member includes an intermediate portion in which the first surface has a recessed surface portion. The intermediate portion defines a hole extending from the recessed surface portion to the second surface. End portions extend from the intermediate portion, and each end portion defines a hole extending from the first surface to the second surface. The member has a tapered surface portion on the second surface. The surgical device includes a second member sized to be received within the recessed surface portion. A method includes locating a tissue fixation device at an opening to a bone hole, and increasing the size of the tissue fixation device by placing the tissue fixation device within a larger device.

16 Claims, 8 Drawing Sheets

(56) References Cited

U.S. PATENT DOCUMENTS

| | | |
|---|---|---|
| 5,741,281 A | 4/1998 | Martin |
| 5,769,894 A | 6/1998 | Ferragamo |
| 6,056,752 A | 5/2000 | Roger |
| 6,086,591 A | 7/2000 | Bojarski |
| 6,193,754 B1 | 2/2001 | Seedhom |
| 6,352,603 B1 | 3/2002 | Bryant |
| 6,517,578 B2 | 2/2003 | Hein |
| 6,533,802 B2 | 3/2003 | Bojarski et al. |
| 6,585,769 B1 | 7/2003 | Muhanna et al. |
| 6,902,573 B2 | 6/2005 | Strobel et al. |
| 2002/0147463 A1* | 10/2002 | Martinek ............ 606/232 |
| 2004/0015171 A1 | 1/2004 | Bojarski et al. |
| 2005/0038427 A1 | 2/2005 | Perriello et al. |
| 2005/0070906 A1* | 3/2005 | Clark et al. ............ 606/72 |

OTHER PUBLICATIONS

International Search Report and Written Opinion for International Application No. PCT/US2006/062456, mailed Jul. 23, 2007.
US 6,238,418, 05/2001, Schwartz et al. (withdrawn)

* cited by examiner

TISSUE GRAFT FIXATION

CROSS-REFERENCE TO RELATED APPLICATIONS

This application is a divisional of U.S. patent application Ser. No. 11/313,716, now U.S. Pat. No. 8,323,338, filed on Dec. 22, 2005, entitled TISSUE GRAFT FIXATION. The contents of the prior application are incorporated herein by reference in their entirety.

TECHNICAL FIELD

This invention relates to tissue graft fixation.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

It is also known to use a graft fixation member, e.g., a fixation button, to secure the tissue graft at the femoral cortex, as described in U.S. Pat. No. 5,306,301 ("the '301 patent") hereby incorporated by reference in its entirety. When using a fixation button, the femoral passage generally includes a relatively larger diameter portion for receiving the graft, and a smaller diameter, passing channel near the femoral cortex for receiving a length of suture that runs from the tissue graft to the fixation button. By measuring the total length of the femoral passage and the length of the larger diameter portion of the femoral passage, the surgeon determines the appropriate length of suture material for attaching the fixation button to the tissue graft.

SUMMARY

According to one aspect, a surgical device includes a member having first and second opposing surfaces. The member includes an intermediate portion in which the first surface has a recessed surface portion. The intermediate portion defines a hole extending from the recessed surface portion to the second surface. End portions extend from the intermediate portion, and each end portion defines a hole extending from the first surface to the second surface.

Embodiments of this aspect may include one or more of the following features.

The surgical device includes a second member sized to be received within the recessed surface portion. The intermediate portion defines two additional holes extending from the recessed surface portion to the second surface. The member has a tapered surface portion on the second surface. The intermediate portion hole is elongated.

According to another aspect, a surgical device includes first and second members. The first member has first and second opposing surfaces, a recessed surface portion in the first surface, and a hole extending from the recessed surface portion to the second surface. The second member defines a hole and is configured to be received within the recessed portion of the first member.

Embodiments of this aspect may include one or more of the following features.

The holes are positioned to be axially aligned when the second member is received within the recessed portion. The recessed portion is configured to provide a snap-fit or an interference-fit with the second member. The surgical device includes a suture extending through the holes. The first member defines at least two additional holes, for example, a total of five holes. The second member defines three additional holes. The first member has a tapered surface portion on the second surface of the member.

According to another aspect, a method includes locating a tissue fixation device at an opening to a bone hole, the tissue fixation device being coupled to a tissue graft by a flexible member, for example, suture, and increasing the size of the tissue fixation device by placing the tissue fixation device within a larger device having a hole for receiving the flexible member. This aspect may include increasing the size of the tissue fixation device prior to locating the tissue fixation device at the opening.

Advantages may include one or more of the following: the continuation of an endoscopic procedure despite perforation of the cortex; use with outside in femoral drilling as is done in pediatric cases to avoid crossing the epiphysis; use as a fast primary to avoid the need for using two drills and measuring of the EndoButton CL length; and coverage of a 6-10 mm tunnel.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
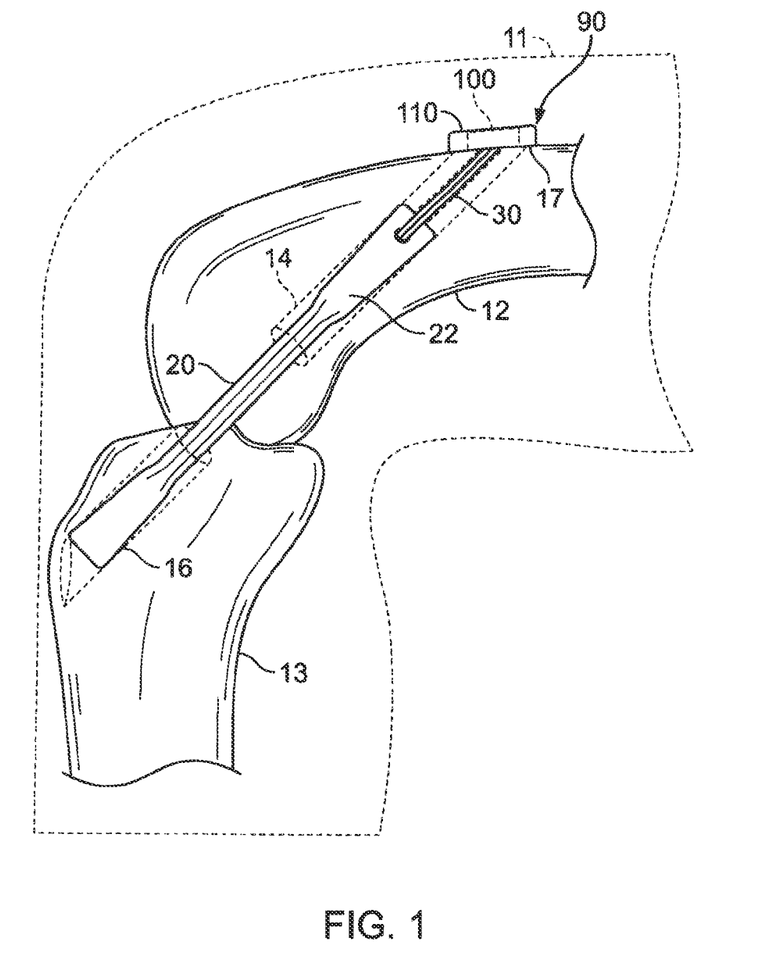
FIG. 1 is an illustration of a tissue graft secured within the knee by a graft fixation member.

Referring to FIG. 1, a fixation member 90 connected to a bone block 22 of a tissue graft 20 by suture 30 is positioned over the opening 17 of a femoral passage 14 to secure the graft 20 in the femoral passage 14. Fixation member 90 includes a first member, e.g., a button 100, received within a second member, e.g., a washer 110. In contrast to techniques that include drilling a passing channel in the femur, such as described in the '301 patent, fixation member 90 enables femoral passage 14 to have a substantially uniform diameter, thus eliminating the added steps of measuring and drilling the relatively smaller passing channel.

Figure 4A:
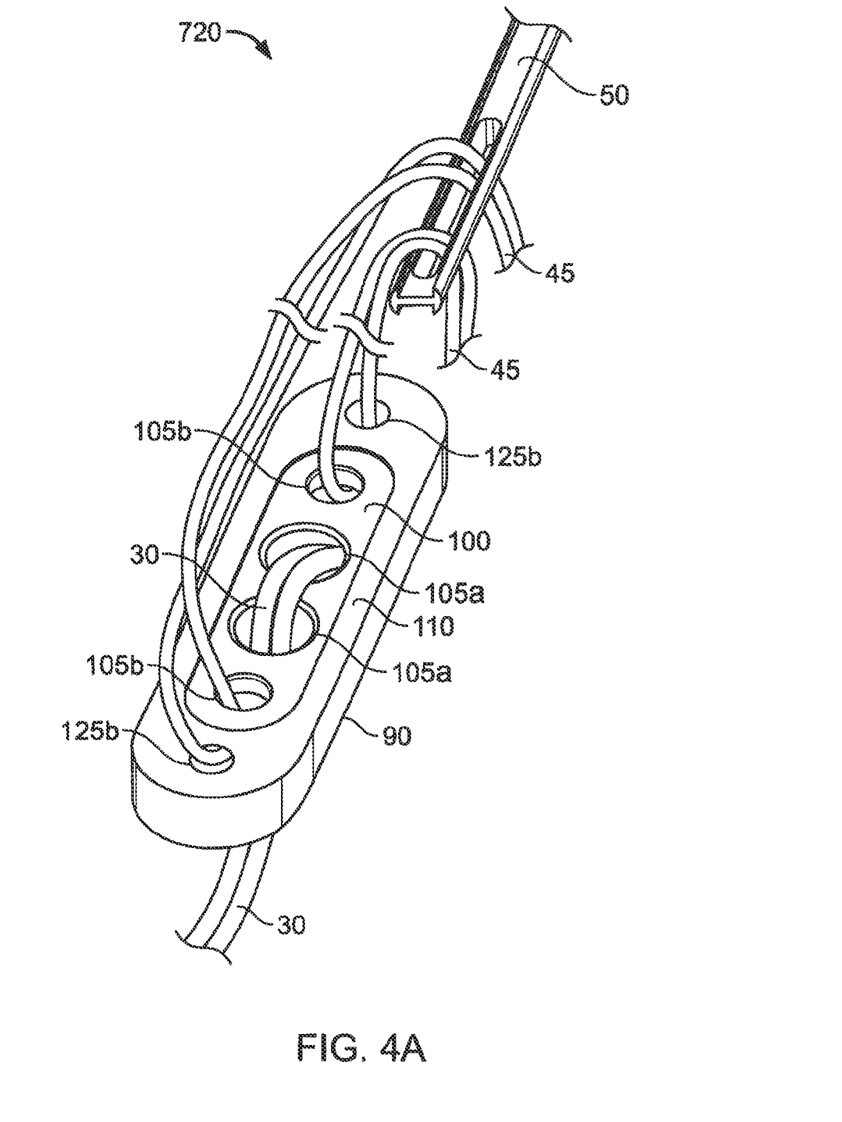
FIG. 4A is a perspective view of the graft fixation member of FIG. 1 shown threaded with suture.

Referring to FIGS. 2A-3B, the washer 110 has a generally elongate shape with an intermediate portion 111 and end portions 112 extending from the intermediate portion 111. Washer 110 has first and second opposing surfaces 114, 115, and the intermediate portion 111 has a recessed surface portion 116 for receiving button 100. Intermediate portion 111 has a hole 120, preferably centrally located, extending from the recessed surface portion 116 to the second surface 115 for receiving the graft tissue suture 30. The washer 110 defines four additional holes 125, one hole 125b in each of the end portions 112, and two inner holes 125a in intermediate portion 111 on either side of central hole 120, for receiving a pull suture 45 (FIG. 4). Holes 125 extend from the first surface 114 to the second surface 115 of the washer.

Figure 7A:
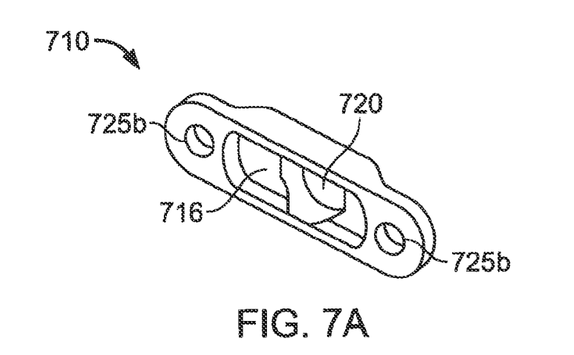
FIG. 7A is perspective view of a washer according to another embodiment.
Figure 7B:
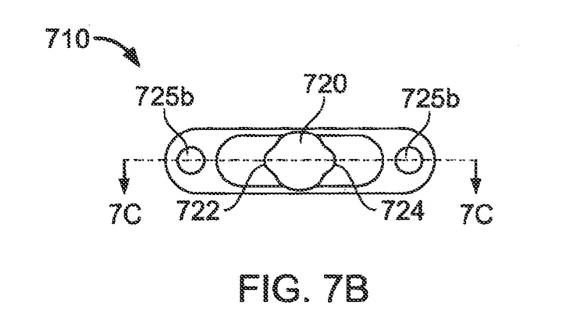
FIG. 7B is a side view of the washer of FIG. 7A.
Figure 7C:
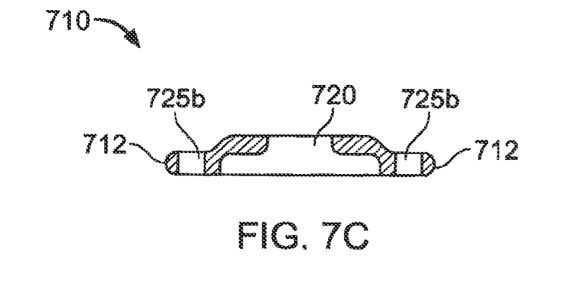
FIG. 7C is a sectional view taken along line 7C-7C in FIG. 7B.
Figure 10A:
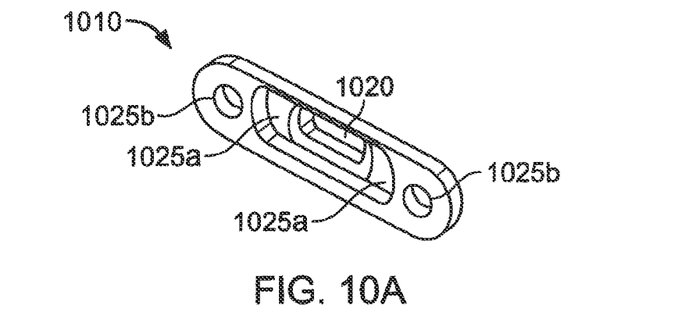
FIG. 10A is perspective view of a washer according to another embodiment.
Figure 10B:
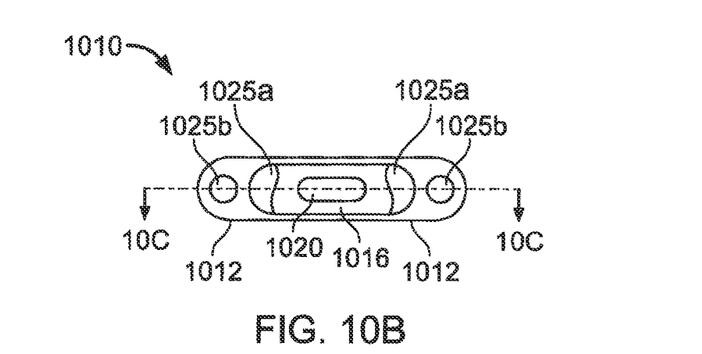
FIG. 10B is an end view of the washer of FIG. 10A.
Figure 10C:
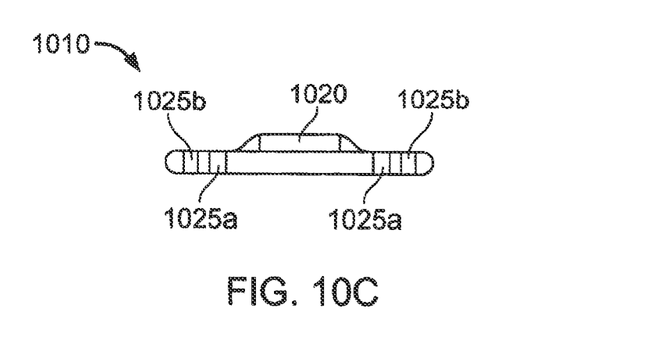
FIG. 10C is a sectional view taken along line 10C-10C in FIG. 10B.

The washer surface 115 is tapered from end portions 112 to intermediate portion 111 (such as shown in FIG. 7C), and can also be tapered along the entire distance between end portions 112 and the intermediate portion 111 as shown in FIGS. 7C and 10C. It is the intermediate portion 111 of the washer that is received within the opening 17 of the femoral passage 14 during use with the washer surface 115 facing the femoral passage. The taper permits fixation member 90 to securely engage the opening 17 of the femoral passage 14 with the washer end portions 112 against the bone surface, while maintaining a low profile relative to bone surface. The taper facilitates a tight fit between the fixation member 90 and passage openings 17 having a range of diameters. Thus, the tapered reduces the need to precisely match the size of the graft fixation member with the femoral passage opening. However, the washer need not include the tapered portion.

Figure 2A:
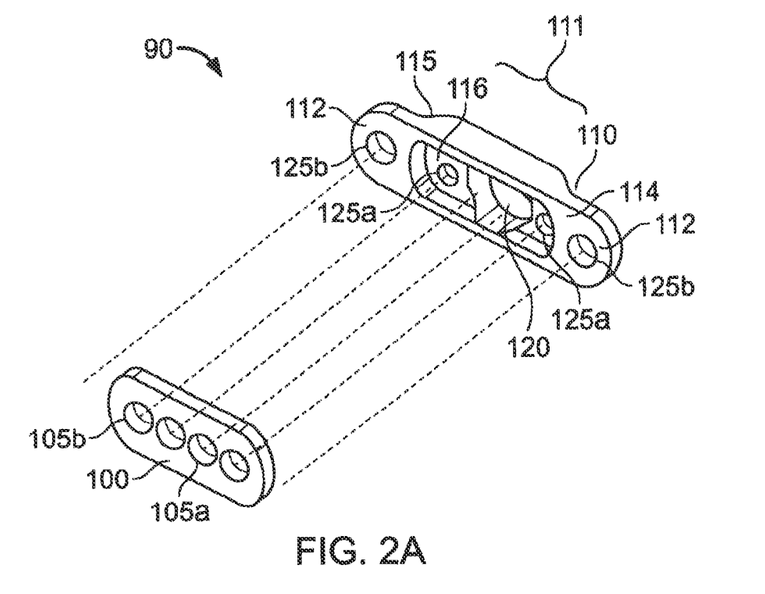
FIG. 2A is an exploded, perspective view of the graft fixation member of FIG. 1.
Figure 2B:
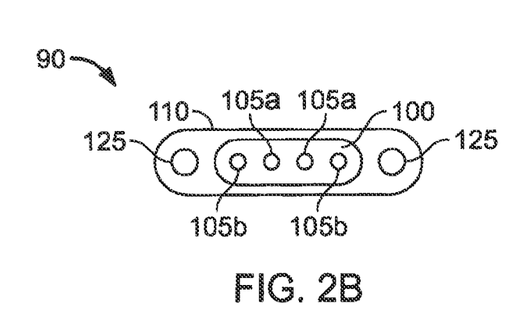
FIG. 2B is an end view of the graft fixation member of FIG. 1.
Figure 3A:
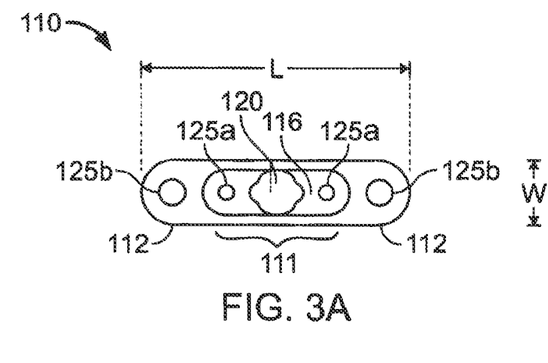
FIG. 3A is an end view of a washer of the graft fixation member of FIG. 1.
Figure 3B:
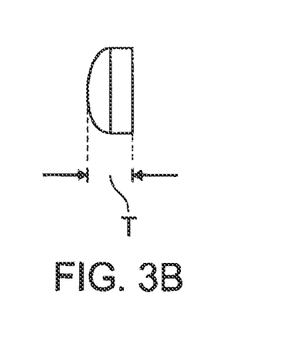
FIG. 3B is a side view of the washer of FIG. 3A.

The button 100 defines holes 105, four holes being shown. The two central holes 105a align with the washer central hole 120, and the two end holes 105b each align with one of the inner washer holes 125a when the button 100 is positioned within the washer recess 116. The elongated washer 110 has a length L, a width W and a thickness T, for example, for an adult femur, the washer 110 has a length of about 15-30 mm, for example, 20 mm, a width of about 6-10 mm, for example, 6 mm, and a thickness of about 1-4 mm, for example, 3 mm, to bridge the span of a femoral passage 14 and provide sufficient rigidity to adequately tension sutures holding a tissue graft 20 while maintaining a relatively low profile with respect to the surface of the femur 12. The washer recess 116 is dimensioned to receive the button 100 by, for example, a snap-fit or interference-fit, and has a depth corresponding to the thickness of the button such that the button is flush with the surface 114 of the washer 110.

Figure 4B:
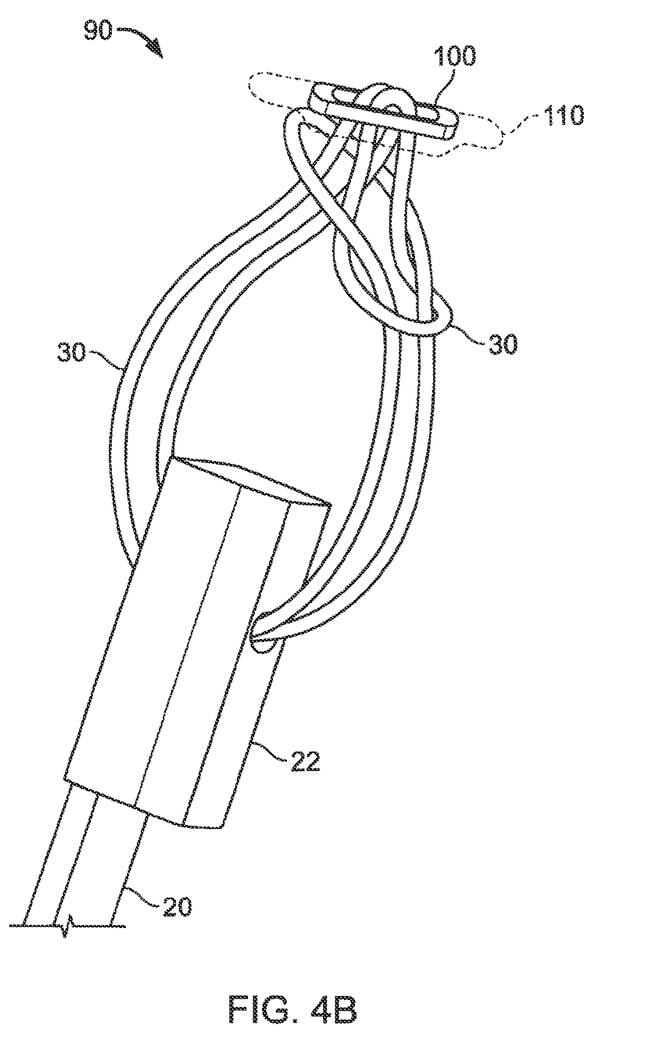
FIG. 4B is an illustration of the graft fixation member coupled to a tissue graft, with the washer shown in dashed line.
Figure 6:
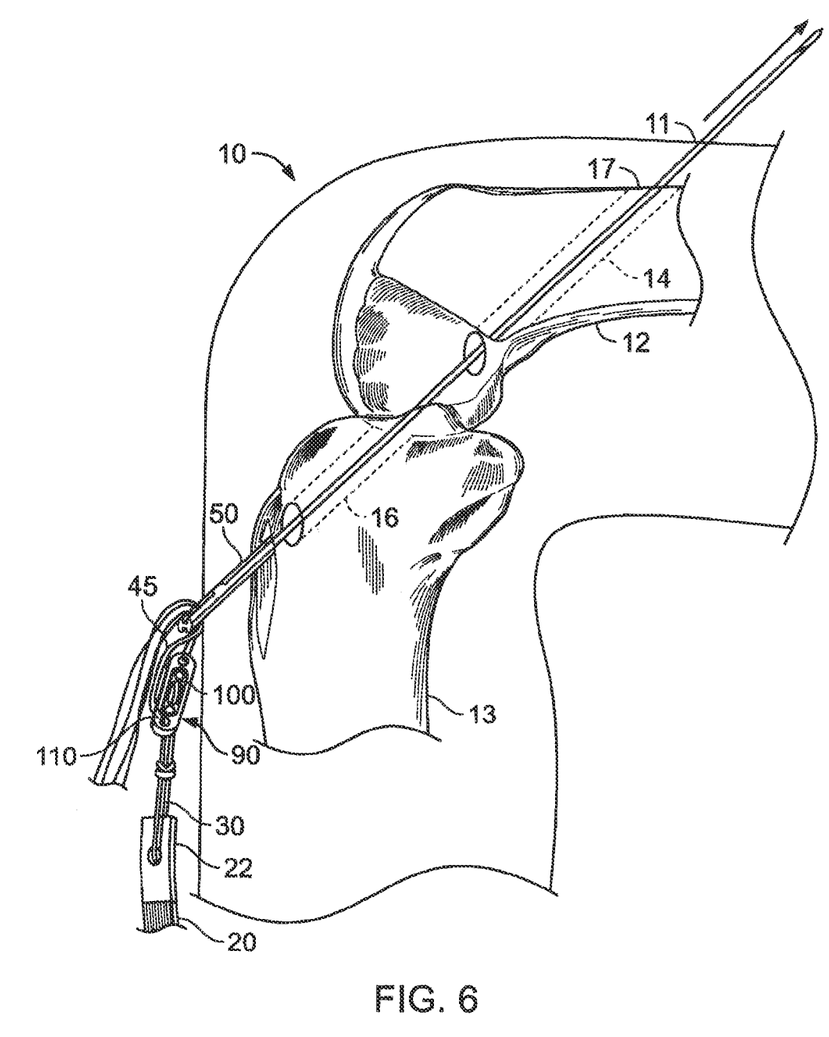
FIG. 6 shows engagement of the graft fixation member with a suture retrieval device for pulling the graft fixation member through the femoral passage.

Referring to FIGS. 4A and 4B, the button 100/washer 110 combination is provided with two closed loops of suture 30 extending through washer hole 120 and threaded through button holes 105a. Graft fixation member 90 is also provided with one suture 45 threaded through one of the washer holes 125b, back through the adjacent washer hole 125a, and through the corresponding button hole 105b, and a second suture 45 similarly threaded through the holes on the other side of the washer and button. Alternatively, operating room personnel can thread the sutures 45. FIG. 6 shows an alternative threading of sutures 45, with one suture 45 threaded through each of the washer holes 125b. Here, washer holes 125a and button holes 105b are not used.

Figure 5:
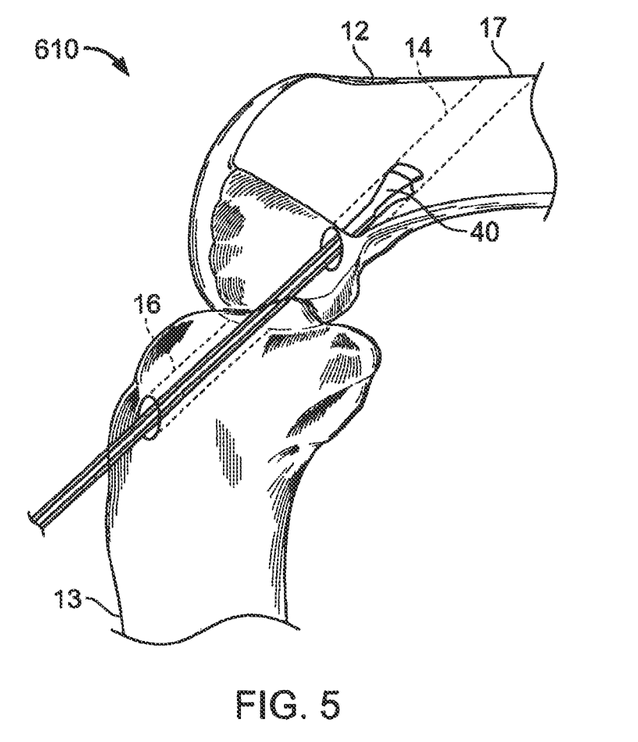
FIG. 5 illustrates drilling a femoral passage within a knee.

Referring to FIGS. 5 and 6, in use, a femoral hole 17 of substantially uniform diameter is drilled using a drill 40. To pull the graft fixation member 90 and tissue graft 20 through the tibia and femur passages, a suture retrieving device, such as a passing pin 50, is used to removably engage the free ends of sutures 44 and pull the fixation member 90 through the knee 10.

Referring to FIG. 1, once the fixation member 90 has been pulled through the femoral passage 14, the surgeon positions the fixation member 90 transversely to the femoral passage 14 and across the opening 17. To complete the fixation of the tissue graft, the fixation member 90 is secured against the femur 12 by attaching the tissue graft 20 to the tibia 13 and tensioning the tissue graft 20 and the closed-loop suture 30 according to methods described in the '301 patent.

Other embodiments are within the scope of the following claims. For example, other embodiments can include washers appropriately sized and shaped to receive buttons with a variety of geometries. Referring to FIGS. 7A-7C, rather than including both the central hole 120 and suture holes 125a within the recess 116, a washer 710 includes only a central hole 720 within a recess 716 sized and shaped to accommodate suture from the four holes 105a and 105b of the button. Hole 720 includes two side extending openings 722, 724 for receiving suture from holes 105b. The washer 710 includes suture holes 725b in end portions 712 of the washer 710.

Figure 8:
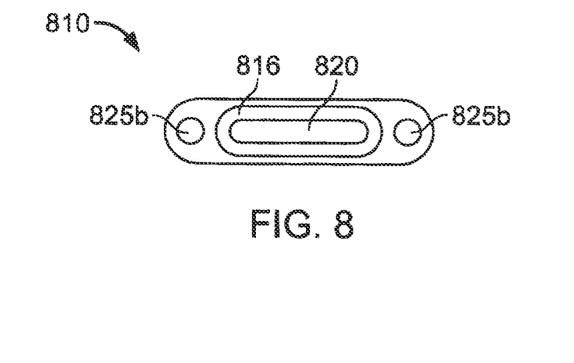
FIG. 8 is a side view of a washer according to another embodiment.
Figure 9:
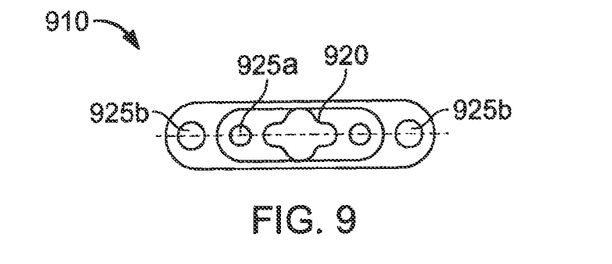
FIG. 9 is a side view of a washer according to another embodiment.

Referring to FIG. 8, in another embodiment, a washer 810 includes only an elongated, central hole 820 within a recess 816, and side holes 825B. Referring to FIG. 9, in another embodiment, a washer 910 includes a central hole 920 and side holes 925B, analogous to holes 720 and 725b in washer 710, but additionally includes holes 925a. In another embodiment (FIGS. 10A-10C), a washer 1010 includes round suture holes 1025b in end portions 912, and oblong suture holes 1025 at recess portion 1016 adjacent to a central hole 1020.

Although the aforementioned embodiments have been described in connection with procedures having a single, uniformly-sized femoral passage, the graft fixation member can be applied to procedures in which a smaller passing channel is formed in the femoral passage. For example, the creation of a smaller passing channel may be desirable in some patients, such as child whose bones are growing or an elderly patient without sufficient bone density to accommodate a relatively large femoral passage 14. In these cases, the graft fixation member advantageously increases the surface area of the bone over which tension is applied.

The recess of the washer can be sized and shaped to completely or partially receive the button. Washers can be provided having different sized and/or shaped recesses to accommodate different buttons. For example, the recessed portion 116 of washer 110 can be sized and shaped to receive the fixation buttons described in U.S. Pat. No. 6,533,802 and U.S. patent application Ser. No. 10/895,266, filed Jul. 20, 2004, published as US 2005-0038427 A1, both incorporated herein in their entirety.

The closed-loop suture 30 can be, but is not limited to, a continuous loop made from polyester, a strand of suture tied in a loop, or a piece of polyester closure tape (e.g. Marselene™ from Ethicon Inc., Cincinnati, Ohio) tied in a loop.

The graft fixation member is formed from a biocompatible material such as titanium or PEEK.

The fixation member can be used with tissue grafts other than those with bone blocks, for example, harvested tissue graft without bone blocks, and tissue grafts formed from synthetic materials or from a combination of synthetic and natural materials.

A number of embodiments have been described. Nevertheless, it will be understood that various modifications may be made. For example, the aforementioned tissue graft fixation procedure may be applicable to other parts of the knee or other parts of the human body requiring tissue reconstruction. Accordingly, other embodiments are within the scope of the following claims.

What is claimed is:

1. A method, comprising:
   locating a tissue fixation device at an opening to a bone hole, the tissue fixation device being coupled to a tissue graft by a flexible member, and
   increasing a size of the tissue fixation device by placing the tissue fixation device within a larger device having a hole for receiving the flexible member, wherein increasing the size comprises increasing the size of the tissue fixation device prior to locating the tissue fixation device at the opening;
   wherein the larger device comprises end portions extending from an intermediate portion and wherein a gradual taper is located along an entire distance between each end portion and the intermediate portion; and
   wherein at least a portion of the gradual taper is linear.

2. The method of claim 1, wherein the flexible member comprises suture.

3. The method of claim 1, wherein the bone hole comprises a femoral passage.

4. The method of claim 3 comprising drilling the femoral passage such that the femoral passage has a substantially uniform diameter.

5. The method of claim 1 comprising passing the tissue fixation device and the tissue graft through the bone hole.

6. The method of claim 1, wherein locating the tissue fixation device at the opening to the bone hole comprises locating the intermediate portion of the larger device at the opening such that a portion of the intermediate portion is received within the opening to the bone hole.

7. The method of claim 6, wherein the intermediate portion defines a planar surface that is substantially parallel to a first surface of the larger device.

8. The method of claim 1, wherein the larger device defines a recessed surface portion and increasing the size of the tissue fixation device comprises placing the tissue fixation device into the recessed surface portion of the larger device.

9. The method of claim 8, wherein the recessed surface portion is adapted to completely or partially receive the tissue fixation device therein.

10. The method of claim 8, wherein the recessed surface portion is dimensioned such that when the tissue fixation device is received within the recessed surface portion a surface of the tissue fixation device is substantially flush with a surface of the larger device.

11. The method of claim 8, wherein the larger device comprises an intermediate portion and end portions extending from the intermediate portion and wherein a gradual taper is located along an entire distance between each end portion and the intermediate portion.

12. The method of claim 11, wherein at least a portion of the gradual taper is linear.

13. The method of claim 11, wherein the intermediate portion defines a planar surface that is substantially parallel to a first surface of the larger device.

14. The method of claim 8, wherein the recessed surface portion is adapted to provide an interference-fit or snap-fit with the tissue fixation device.

15. The method of claim 1, wherein the tissue fixation device is placed within the larger device such that a surface of the tissue fixation device is substantially flush with a surface of the larger device.

16. A method, comprising:
   locating a tissue fixation device at an opening to a bone hole, the tissue fixation device being coupled to a tissue graft by a flexible member, and
   increasing a size of the tissue fixation device by placing the tissue fixation device within a larger device having a hole for receiving the flexible member;
   wherein the tissue fixation device defines a plurality of through holes for receiving one or more flexible members;
   wherein the larger device comprises end portions extending from an intermediate portion and wherein a gradual taper is located along an entire distance between each end portion and the intermediate portion; and
   wherein at least a portion of the gradual taper is linear.

* * * * *